(12) United States Patent
Furnish et al.

(10) Patent No.: US 10,881,846 B2
(45) Date of Patent: *Jan. 5, 2021

(54) MEDICAL VALVE WITH A VARIABLE DIAMETER SEAL

(71) Applicant: FREUDENBERG MEDICAL, LLC, Carpinteria, CA (US)

(72) Inventors: Greg Furnish, Louisville, KY (US); Anthony Appling, Crestwood, KY (US); Ben Morris, Jeffersonville, IN (US); Timothy S. Zeis, Charlestown, IN (US)

(73) Assignee: FREUDENBERG MEDICAL, LLC, Carpinteria, CA (US)

( * ) Notice: Subject to any disclaimer, the term of this patent is extended or adjusted under 35 U.S.C. 154(b) by 264 days.

This patent is subject to a terminal disclaimer.

(21) Appl. No.: 15/966,173

(22) Filed: Apr. 30, 2018

(65) Prior Publication Data

US 2018/0256876 A1 Sep. 13, 2018

Related U.S. Application Data

(63) Continuation-in-part of application No. 15/483,089, filed on Apr. 10, 2017, now abandoned, which is a
(Continued)

(51) Int. Cl.
*A61M 39/02* (2006.01)
*A61M 39/06* (2006.01)
(Continued)

(52) U.S. Cl.
CPC ..... *A61M 39/0613* (2013.01); *A61B 1/00137* (2013.01); *A61B 1/018* (2013.01);
(Continued)

(58) Field of Classification Search
CPC .............. A61M 39/0613; A61M 39/10; A61M 2039/062; A61M 2039/0633; A61M 2039/0673
See application file for complete search history.

(56) References Cited

U.S. PATENT DOCUMENTS

| 5,484,418 A | 1/1996 | Quiachon et al. |
| 5,634,908 A | 6/1997 | Loomas |

(Continued)

FOREIGN PATENT DOCUMENTS

| EP | 0426407 A2 | 5/1991 |
| EP | 2965685 A1 | 1/2016 |

(Continued)

OTHER PUBLICATIONS

Search Report dated Nov. 23, 2015 in corresponding European Patent Application No. 15175941.2.

*Primary Examiner* — Manuel A Mendez
*Assistant Examiner* — Justin L Zamory
(74) *Attorney, Agent, or Firm* — Dickinson Wright PLLC

(57) ABSTRACT

A medical valve assembly includes a tube extending between a first and second tube end along an axis, and a plunger plate extends radially from the second tube end. A valve housing surrounds the tube and includes a radially inwardly extending flange. A compression member is biased against the plunger plate and compresses an elastomeric seal from a non-compressed condition to a compressed condition to establish a sealed condition of the medical valve assembly. An inner surface of the elastomeric seal in the non-compressed condition has a plurality of planar portions and a plurality of radiused portions, with adjacent planar portions interconnected with one of the radiused portions to improve a closure of the elastomeric seal during compression. The inner surface preferably includes three planar portions and three radiused portions to define a generally
(Continued)

triangular-shaped inner surface as viewed in cross section in the non-compressed condition.

20 Claims, 9 Drawing Sheets

Related U.S. Application Data continuation of application No. 14/326,593, filed on Jul. 9, 2014, now Pat. No. 9,616,213.

(51) Int. Cl.
*A61B 1/00* (2006.01)
*A61B 1/018* (2006.01)
*A61M 39/10* (2006.01)

(52) U.S. Cl.
CPC ....... *A61M 39/10* (2013.01); *A61M 2039/062* (2013.01); *A61M 2039/0633* (2013.01); *A61M 2039/0673* (2013.01)

(56) References Cited

U.S. PATENT DOCUMENTS

| | | | |
|---|---|---|---|
| 5,882,345 A | 3/1999 | Yoon | |
| 6,458,103 B1 | 10/2002 | Albert et al. | |
| 6,572,590 B1 * | 6/2003 | Stevens | A61M 39/0613 604/246 |
| 7,967,790 B2 | 6/2011 | Whiting et al. | |
| 8,025,641 B2 | 9/2011 | Bettuchi | |
| 2004/0178586 A1 | 9/2004 | Junge | |
| 2006/0241671 A1 | 10/2006 | Greenhalgh | |
| 2011/0264105 A1 | 10/2011 | Barthold | |
| 2012/0238958 A1 | 9/2012 | Moore | |
| 2012/0310166 A1 | 12/2012 | Huff | |

FOREIGN PATENT DOCUMENTS

| | | |
|---|---|---|
| EP | 3088039 A1 | 11/2016 |
| JP | 2000316986 A | 11/2000 |
| WO | WO2005058409 A1 | 6/2005 |

\* cited by examiner

MEDICAL VALVE WITH A VARIABLE DIAMETER SEAL

CROSS-REFERENCE TO RELATED APPLICATIONS

This application is a continuation-in-part of U.S. patent application Ser. No. 15/483,089 filed on Apr. 10, 2017, which is a continuation of U.S. patent application Ser. No. 14/326,593 filed on Jul. 9, 2014, now U.S. Pat. No. 9,616,213, the entire disclosures of which are incorporated herein by reference.

BACKGROUND OF THE INVENTION

1. Field of the Invention

The present disclosure relates generally to medical devices and procedures. In particular, the present disclosure relates to hemostatic valves and systems, and methods of using the same.

2. Description of the Prior Art

This section provides background information related to the present disclosure which is not necessarily prior art.

Numerous procedures have been developed that involve the percutaneous insertion of a medical device into a body vessel of a patient, with the medical device being introduced into the vessel by a variety of known techniques. Each of these procedures must control the flow of bodily fluids when the medical device is inserted into the body vessel. Accordingly, medical valves, such as hemostatic valves, iris valves, laproscopic ports, or the like, are often used to limit or prevent blood loss during the procedure.

Hemostatic valves often incorporate a disk valve to control fluid flow through the medical device. However, disk valves are subject to deformation with both time and use, and often can tear or become dislodged during insertion and/or withdrawal of the medical device. Furthermore, disk valves are not designed to provide an effective seal across a wide range of differently sized medical devices. Although the disk valve can be modified to accommodate these situations, such as with increased tensile and/or elongation properties, this modification leads to increased resistance, and thus require the use of excessive force, when the medical device is inserted and withdrawn through the disk valve.

Iris valves can include an elastomeric sleeve that is disposed within a valve body and which is interconnected to a rotatable cap. When the cap is rotated in a first direction, an opening extending through the elastomeric sleeve is opened. Conversely, when the cap is rotated in a second opposite direction, the elastomeric sleeve is twisted and constricted to effectuate a closure of the elastomeric sleeve. However, if the operator stops the rotation, the elastomeric sleeve can revert, or recoil, back to the open position. Additionally, even when the elastomeric sleeve is held in the closed position, gaps or channels extend therethrough as a result of the twisting or infolding required to effectuate a closure. Accordingly, fluid can leak through the iris valve in the closed position. Further, the continuous twisting and constricting of the elastomeric sleeve leads to wear of the sleeve, such as through tearing.

The drawbacks associated with the existing medical valves are further exemplified when one considers that a single medical valve often is used to insert multiple medical devices during a single procedure. For example, a hemostatic valve may be used first for introducing a delivery catheter, followed by an interventional catheter. In this example, the hemostatic valve must be able to provide a hemostatic seal under a variety of conditions, i.e., accommodate a variety of different sized medical devices. Additionally, the hemostatic valve device must be able to quickly adjust to use of each of these different medical devices, otherwise significant fluid loss can occur through the medical valve.

SUMMARY OF THE INVENTION

This section provides a general summary of the disclosure and is not intended to be a comprehensive disclosure of its full scope, aspects, objectives, and/or all of its features.

A medical valve assembly for use in inserting a medical device into a body vessel of a patient includes a tube extending between a first tube end and a second tube end along an axis. A plunger plate extends radially from the second tube end and a valve housing surrounds the tube about the second tube end. The valve housing extends from a first valve housing end to a second valve housing end and includes a flange extending radially inwardly from the second valve housing end, with the flange disposed in spaced relationship with respect to the plunger plate so as to define a distance dimension therebetween. An elastomeric seal is compressed between the plunger plate and the flange and has an inner surface defining inner diameter for use in establishing a variable seal of the medical valve assembly. A compression member is disposed within the valve housing and is biased against the plunger plate for decreasing the inner diameter of the inner surface to establish a closed condition of the medical valve. The inner surface of the elastomeric seal has a plurality of planar portions and a plurality of radiused portions, with adjacent ones of the plurality of planar portions interconnected with one of the plurality of radiused portions. The inner surface comprised of alternating planar portions and radiused portions provides a more consistent closure of the inner surface along each of the planar surfaces and also allows the inner surface of the elastomeric seal to close shut and seal under less compression—each of which improves performance and reliability of the elastomeric seal in the medical valve assembly.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments, and are not all possible implementations and thus are not intended to limit the scope of the present disclosure.

DESCRIPTION OF THE ENABLING EMBODIMENTS

Example embodiments will now be described more fully with reference to the accompanying drawings. The example embodiments are provided so that this disclosure will be thorough and fully convey the scope to those skilled in the art. Numerous specific details are set forth such as examples of specific components, devices, mechanisms, assemblies, and methods to provide a thorough understanding of various embodiments of the present disclosure. It will be apparent to those skilled in the art that specific details need not be employed, that example embodiments may be embodied in many different forms, and that neither should be construed to limit the scope of the disclosure. With this in mind, the present disclosure is generally directed to medical valve assemblies of the type used to introduce and withdrawal a medical device (i.e., a guide wire, catheter, stent, filter, etc.) into a body vessel of a patient. In particular, each of the medical valve assemblies of the present disclosure incorporate a variable seal arrangement and a manually-operable actuator for controlling an entry dimension of the variable seal arrangement.

Figure 1:
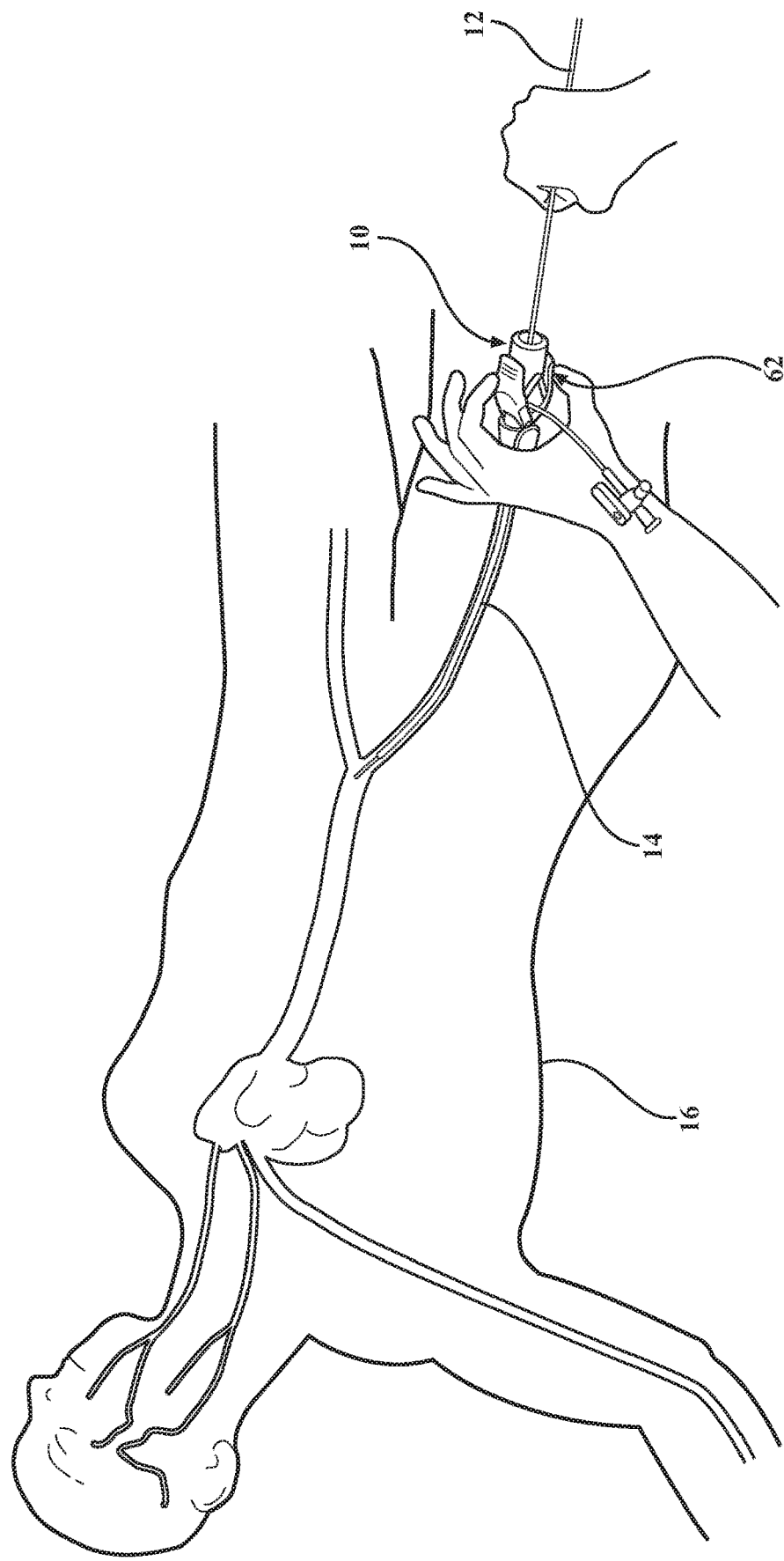
FIG. 1 is an environmental view of a first embodiment of a medical valve constructed in accordance with the principles of the present disclosure and illustrating a user interacting therewith.
Figure 2:
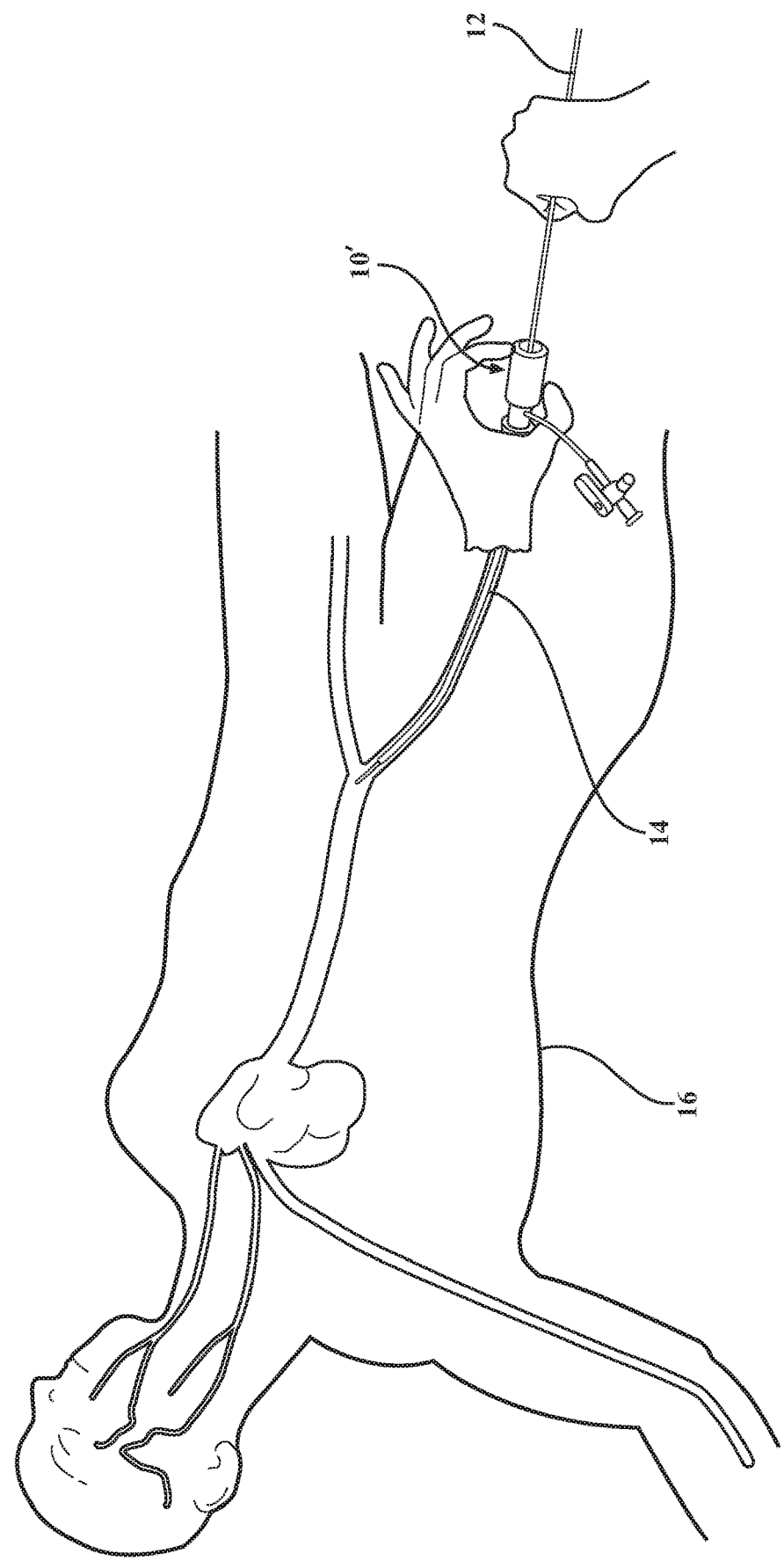
FIG. 2 is an environmental view of a second embodiment of the medical valve constructed in accordance with the principles of the present disclosure and illustrating the user interacting therewith.

Referring to the Figures, wherein like numerals indicate corresponding parts throughout the several views, an environmental view of a first embodiment of a medical valve assembly 10 and a second embodiment of a medical valve assembly 10' is generally shown in FIGS. 1 and 2, respectively. As illustrated therein, each medical valve assembly 10, 10' is of the type for use with a medical device 12, such as a guide wire, catheter, stent, filter, vessel occlusion device, or the like. As will be explained in more detail below, as the medical device 12 is inserted and guided through the medical valve assembly and into a body vessel 14 of a patient 16, a user can manually actuate or interact with the medical valve assembly to effectuate a variable seal with a variety of different sized medical devices 12.

As best shown in FIGS. 4A, 4B, 9, 11A and 11B, the medical valve assemblies 10, 10' each include a tube 20 extending between a first tube end 22 and a second tube end 24 to define a passageway 26 extending longitudinally along an axis A between the ends 22, 24, with the passageway 26 being sized to receive a variety of differently sized medical devices 12. In this instance, the first tube end 22 is a distal tube end and the second tube end 24 is a proximal tube end 24. A plunger plate 28 extends radially from the second tube end 24 to define an outer plunger plate surface 30 extending in spaced and parallel relationship to the axis A. A valve housing 32 is disposed in surrounding relationship with the tube 20 about the second tube end 24 and extends from a first valve housing end 34 to a second valve housing end 36 to overlay the outer plunger plate surface 30. In this instance, the first valve housing end 34 is a distal valve housing end and the second valve housing end 36 is a proximal valve housing end 36. As best shown in FIGS. 4A, 4B, 9, 11A and 11B, the valve housing 32 is disposed in spaced and parallel relationship with the tube 20 between the first valve housing end 34 and the plunger plate 28.

The valve housing 32 includes a flange 38 extending radially inwardly from the second valve housing end 36. The flange 38 is disposed in spaced relationship with the plunger plate 28 to define a distance dimension D, as well as a cavity 40, extending therebetween. The flange 38 also defines an opening 42 aligned on the axis A and that is sized to receive a variety of differently sized medical devices 12. An elastomeric seal 44 is installed in the cavity 40 and normally is pre-loaded or compressed between the plunger plate 28 and the flange 38. The elastomeric seal 44 has an inner surface 45 which is used to establish a variable seal of the medical valve assembly 10, 10'. In both of the first and second embodiments of the medical valve assembly 10, 10', one of the valve housing 32 or the tube 20 is axially movable relative to the other to vary the distance dimension D between the plunger plate 28 and the flange 38 for effectuating an adjustment of an inner diameter 46 as defined by the inner surface 45 of the elastomeric seal 44. In other words, the axial movement of one of the valve housing 32 or the tube 20 relative to the other results in a change in the compression load exerted on the elastomeric seal 44 which, in turn, allows the inner diameter 46 defined by the inner surface 45 of the elastomeric seal 44 to be varied or adjusted in size. As best shown in FIGS. 4A, 4B, 9, 11A and 11B, when the valve housing 32 or the tube 20 is axially moved, the plunger plate 28 or the valve housing 32 axially slides relative to the other along the outer plunger plate surface 30. In other words, the outer plunger plate surface 30 guides a sliding axial movement between the valve housing 32 and the tube 20.

As best shown in FIGS. 4A, 4B, 9, 11A, and 11B, a compression member 48, 54 is disposed within the valve housing 32 and is compressed against the plunger plate 28 for normally closing or decreasing the inner diameter 46 through a compression of the elastomeric seal 44 to establish a closed position or condition of the elastomeric seal 44. As a result, the compression member 48, 54 is arranged to effectuate a closing or decreasing of the inner diameter 46 of the elastomeric seal 44 to establish a closed condition of the medical valve assembly 10, 10'. In its closed condition, the elastomeric seal 44 completely isolates or seals the opening 42 of the valve housing 32 from the passageway 26 of the tube 20. The valve housing 32 or the tube 20 is then axially movable relative to the other to alter a distance D between the flange 38 and the plunger plate 28 and shift the medical valve assembly 10, 10' from the closed condition to an open/operative condition. The altered or varied distance D between the flange 38 and the plunger plate 28 allows the elastomeric seal 44 to expand, and as a result, the inner diameter 46 of the elastomeric seal 44 is expanded or increased to move the elastomeric seal 44 from its closed position to an open position. With the elastomeric seal 44 in its open position, the medical device 12 is positioned to be inserted serially through the opening 42, the inner diameter 46 of the elastomeric seal 44 and the passageway 26 of the medical valve assembly 10.

As best shown in FIGS. 4A, 4B, 11A and 11B, in the first embodiment of medical valve assembly 10, the compression member 48, 54 comprises a coil spring 48 radially disposed between the valve housing 32 and the tube 20 and compressed between the first valve housing end 34 and the plunger plate 28. However, any other suitable compression member could be utilized without departing from the scope of the subject disclosure. In a preferred embodiment, a disk 50 is slidably disposed around the tube 20 and interconnected to the first valve housing end 34 to establish a shoulder 52 extending radially inward from the valve housing 32 and which is disposed in engagement with the coil spring 48. The coil spring 48 acts to bias the valve housing 32 towards the first tube end 22 for compressing the elastomeric seal 44 between the flange 38 and the plunger plate 28 and normally position the elastomeric seal 44 in its closed position. The valve housing 32 is then axially movable from the closed position and relative to the tube 20 to increase the distance D between the flange 38 and the plunger plate 28. The increased distance D allows the elastomeric seal 44 to expand in an increased area of the cavity 40 disposed between the flange 38 and the plunger plate 28, and as a result, the inner diameter 46 of the elastomeric seal 44 is expanded or increased, thereby opening the elastomeric seal 44. The result is the establishment of the open condition of the medical valve assembly 10.

Figure 8:
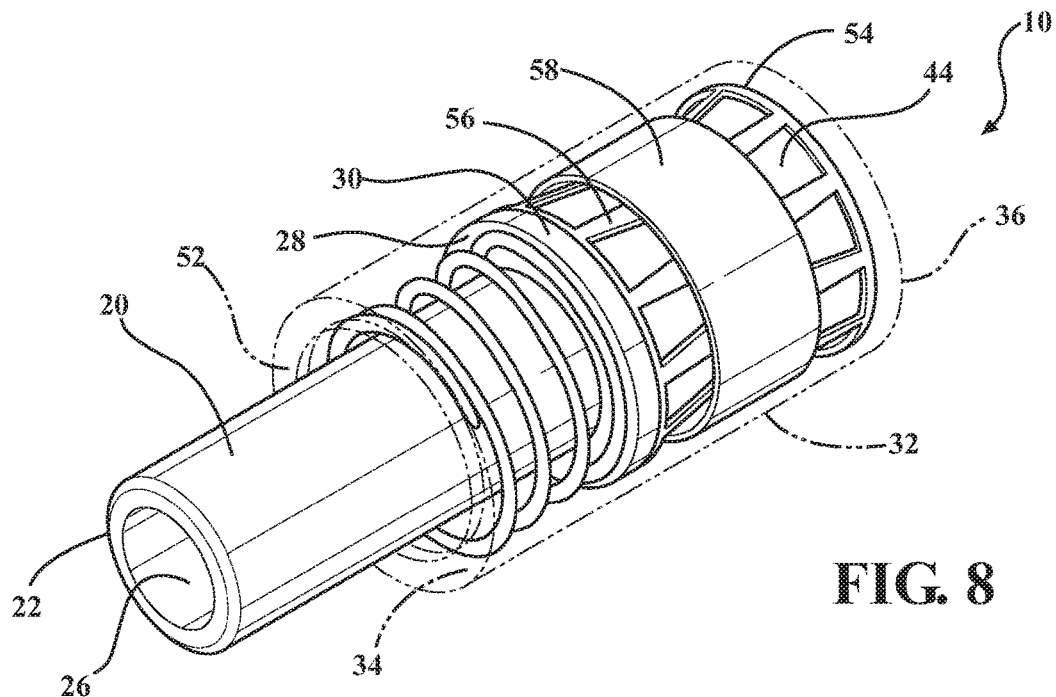
FIG. 8 is a perspective view of the second embodiment of a medical valve constructed in accordance with the present disclosure.
Figure 9:
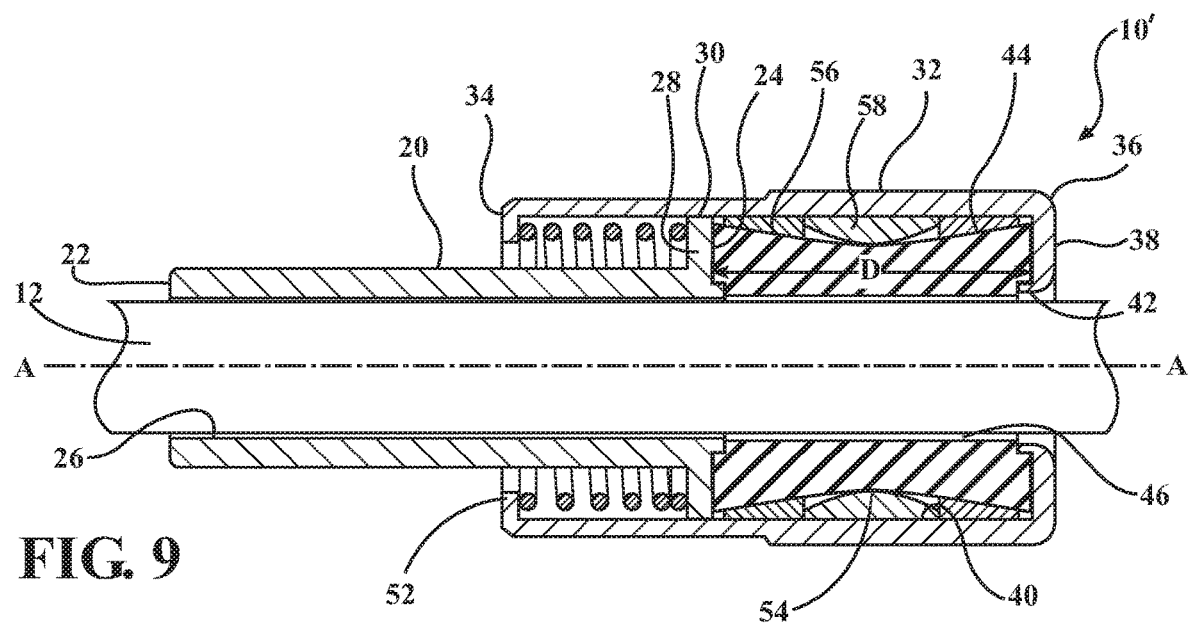
FIG. 9 is a cross-sectional view of the second embodiment shown in FIG. 8.

As best shown in FIGS. 8 and 9, in the second embodiment of the medical valve assembly 10', the compression member 48, 54 also comprises a coil spring 48 radially disposed between the valve housing 32 and the tube 20 and compressed between the first valve housing end 34 and the plunger plate 28. However, any other suitable compression member could be utilized without departing from the scope of the subject disclosure. The valve housing 32 defines a shoulder 52 extending radially inward from the first valve housing end 34 and slidably disposed around the tube 20. The shoulder 52 is disposed in engagement with the coil spring 48, and the coil spring 48 acts to bias the valve housing 36 towards the first tube end 22. In a preferred embodiment, the compression member 48, 54 additionally includes a leaf spring cage 54 disposed in surrounding relationship with the elastomeric seal 44. However, any other suitable compression member could be utilized without departing from the scope of the subject disclosure. The leaf spring cage 54 extends between the plunger plate 28 and the flange 38 and is compressed therebetween by way of the compression spring 48. The leaf spring cage 54 includes a plurality of struts 56 each extending axially along the leaf spring cage 54 and configured to fold radially inward towards the elastomeric seal 44 when the valve housing 36 is axially biased towards the first tube end 22 by the compression spring 48. As a result, the distance D between the plunger plate 28 and the flange 38 is decreased, thus causing the elastomeric seal 44 to compress and reduce the inner diameter 46. Put another way, the coil spring 48 and the leaf spring cage 54 interact to compress the elastomeric seal 44 between the flange 38 and the plunger plate 28 and normally position the elastomeric seal 44 in its closed position. As a medical device 12 is inserted through the passageway 26, the medical device 12 engages the elastomeric seal 44 with an insertion force that is transferred or exerted radially outward on the struts 56 of the leaf spring cage 54, causing the leaf spring cage 54 to expand and counteract the biasing force of the coil spring 48. As a result, the distance between the plunger plate 28 and the flange 38 is increased, allowing the inner diameter 46 of the elastomeric seal 44 to expand or increase and establish the open condition of the medical valve assembly 10'. A constrictor band 58 extends around the leaf spring cage 54 to prevent the plurality of struts 56 from engaging the valve housing 32 when the leaf spring cage 54 is expanded by the insertion force of the medical device 12.

Figure 6:
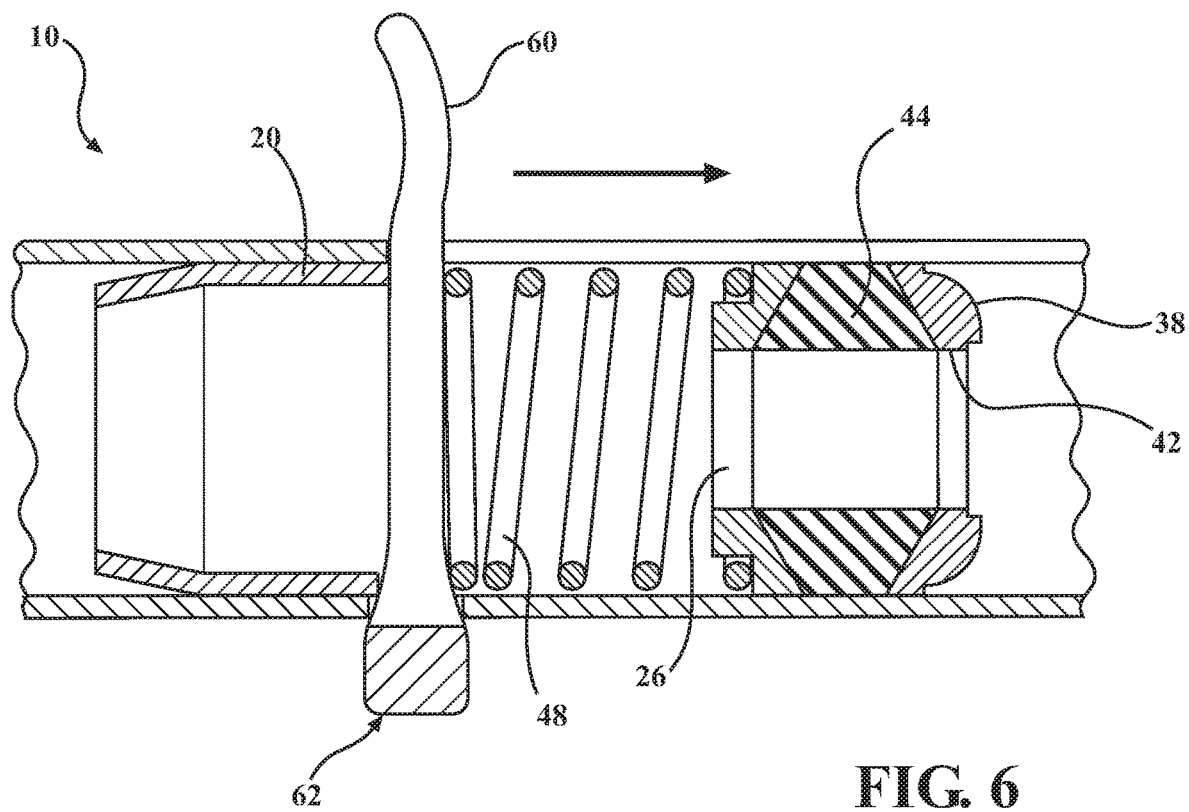
FIG. 6 is a cross-sectional view of the first embodiment of the medical valve illustrating an alternative arrangement for the manual actuator.

As best shown in FIGS. 3, 4A, 4B, 11A and 11B, the first embodiment of the medical valve assembly 10 includes a manual actuator 62 which can be connected to the valve housing 32 for allowing a user to interact with the medical valve assembly 10 and vary a size of the inner diameter 46 of the elastomeric seal 44. Put another way, the user can interact with the manual actuator 62 to overcome the bias of the compression member 48 and move the valve housing 32 relative to the tube 20 along the axis A towards the second tube end 24. As a result, the manual actuator 62 allows the user to manually establish the open condition of the medical valve assembly 10. As best shown in FIG. 6, in the alternative embodiment, the manual actuator 62 can include a trigger arm 60 extending radially from the valve housing 32. In this situation, the user can pull back on the trigger arm 60 to establish the open condition of the medical valve assembly 10. In other words, a user can pull back the trigger arm 60 to vary the bias on the plunger plate 28.

Figure 3:
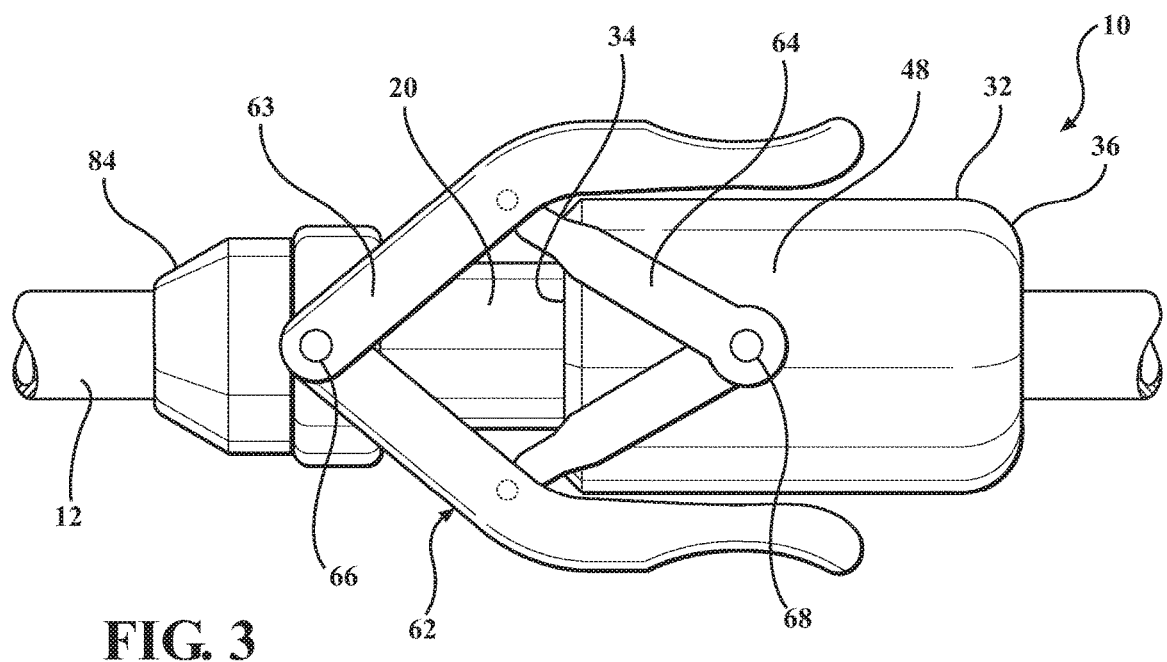
FIG. 3 is a perspective view of the first embodiment of the medical valve illustrating a scissor-type manual actuator.
Figure 4A:
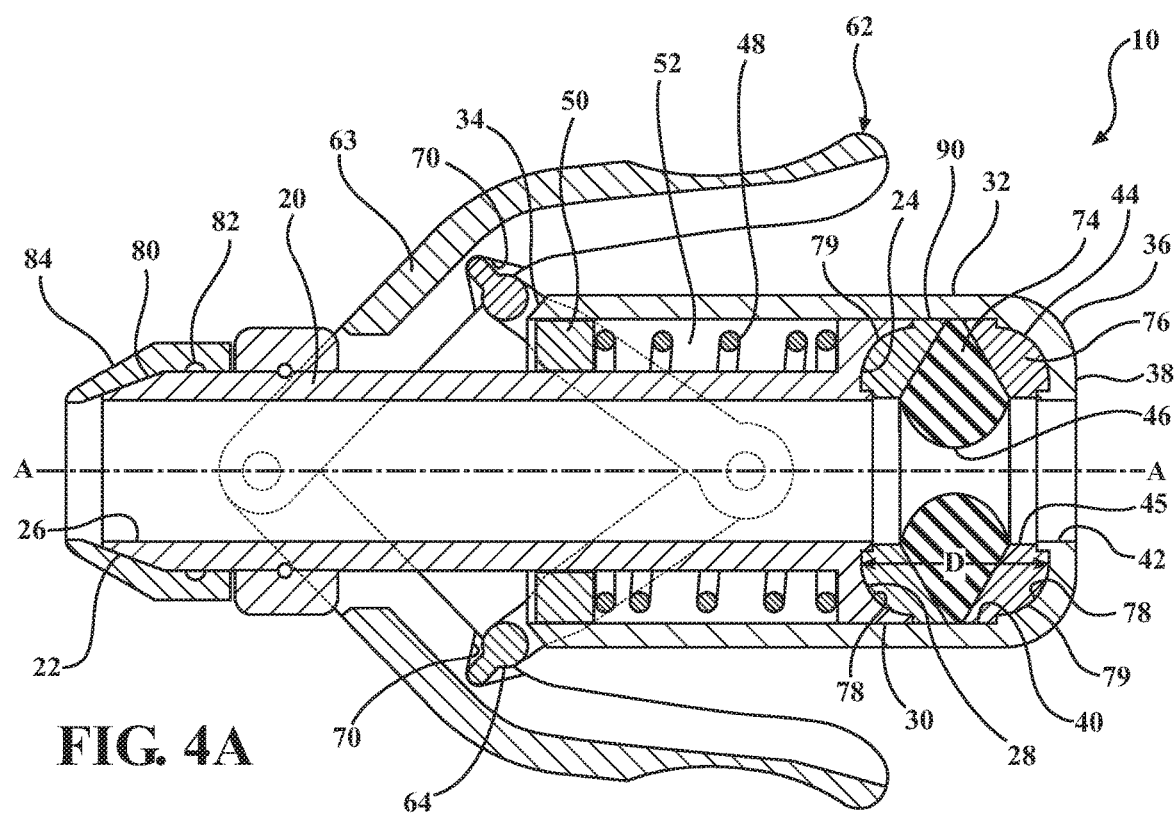
FIG. 4A is a cross-sectional view of the first embodiment of the medical valve illustrating a closed condition.
Figure 4B:
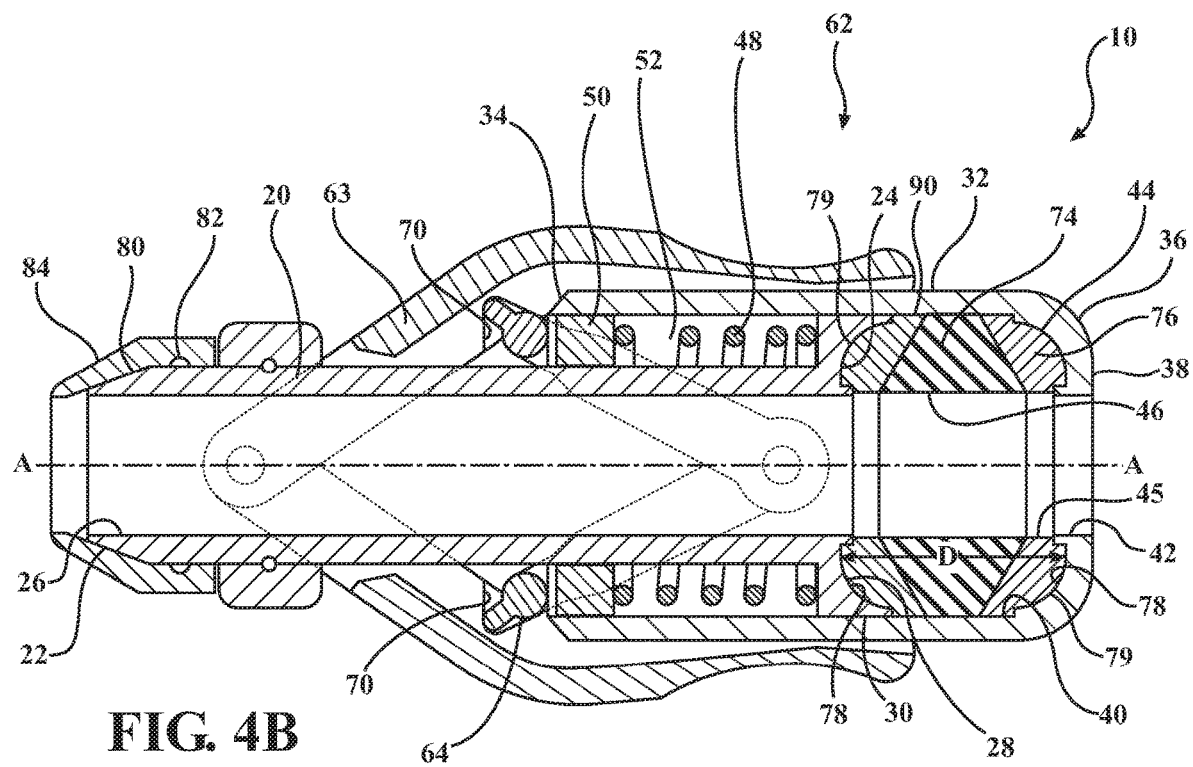
FIG. 4B is a cross-sectional view of the first embodiment of the medical valve illustrating an open condition.
Figure 7:
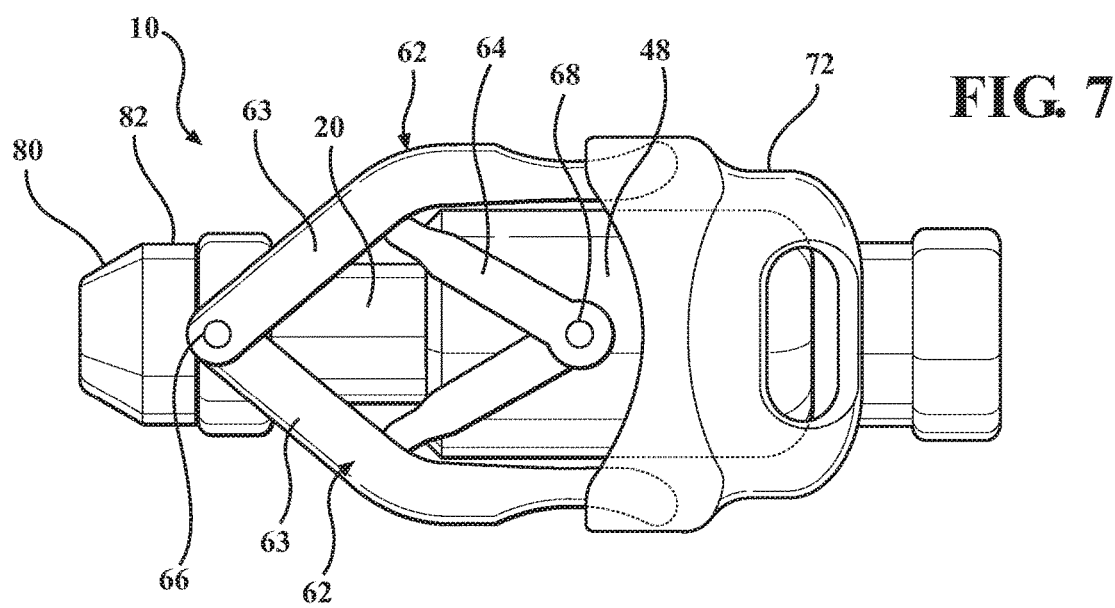
FIG. 7 is a perspective view of the first embodiment illustrating a detachable cap disposed over a pair of lever arms associated with the scissor-type manual actuator.

As best shown in FIGS. 3, 4, 11A and 11B, the manual actuator 62 can include a pair of lever arms 63 interconnected between the tube 20 and the valve housing 32 by way of a pair of lever linkages 64. As best shown in FIG. 3, each lever arm 63 includes a first pivot 66 extending radially from the tube 20 and each lever linkage 64 includes a second pivot 68 extending radially from the valve housing 32. The pair of lever arms 63 are pivotably connected to the tube 20 by the first pivots 66 and the pair of lever linkages 64 are pivotably connected to the valve housing by the second pivots 68 with each of the lever linkages 64 extending from the respective second pivot 68 to engage one of the respective lever arms 63. As best shown in FIG. 7, in a preferred embodiment, each of the lever arms 63 can also define a track 70 for receipt of the respective lever linkage 64 when the lever linkages 64 are disposed in abutting relationship with the lever arms 63. This arrangement of the lever arms 63 and the lever linkages 64 allows the user to squeeze or compress the pair of lever arms 63 with a specific force to axially advance the valve housing 32 by way of the lever linkages 64. As a result, the transferred force effectuates the increase in the distance D between the plunger plate 28 and the flange 38, and thus the increase in the inner diameter 46 of the elastomeric seal 44. Put another way, a user can radially squeeze or compress the lever arms 63 to release compression on the elastomeric seal 44 and increase the inner diameter 46 of the elastomeric seal 44 from the closed condition to a desired size of the inner diameter 46 based on an amount of radial squeeze.

Figure 10:
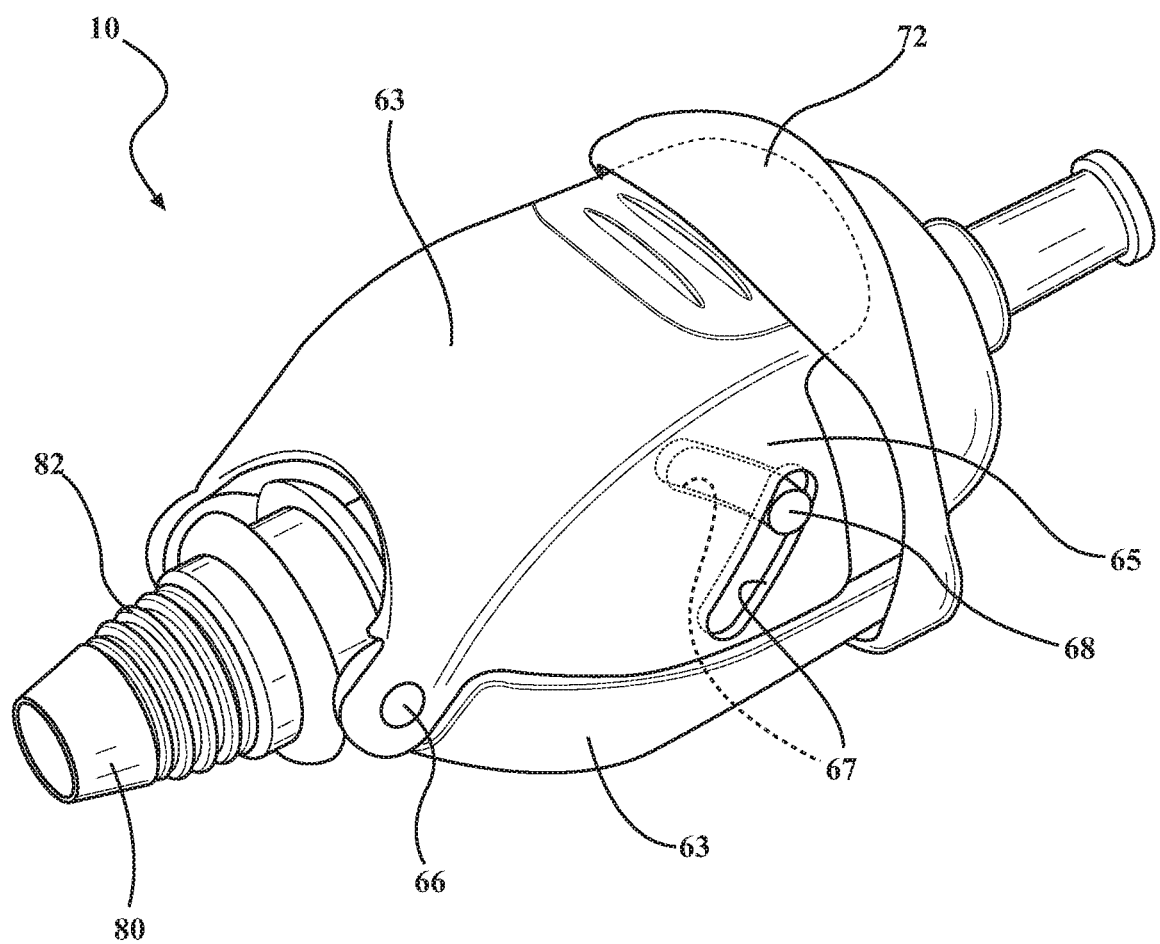
FIG. 10 is a perspective view of the first embodiment illustrating an alternative arrangement of the scissor-type manual actuator.

As best shown in FIG. 10, in an alternative arrangement the pair of lever arms 63 can be interconnected between the tube 20 and the valve housing 32 by way of a pair of plates 65. In a preferred embodiment, each lever arm 63 includes a plate 65 which extends radially therefrom and which defines a cam slot 67 for receiving the second pivot 68 extending radially from the valve housing 32. This arrangement of the lever arms 63 and the plates 65 allows the user to squeeze or compress the pair of lever arms 63 with a specific force to slide the second pivot 68 along the cam slots 67 and axially advance the valve housing 32 by way of the plates 65. As a result, the transferred force effectuates the increase in the distance D between the plunger plate 28 and the flange 38, and thus the increase in the inner diameter 46 of the elastomeric seal 44. Put another way, a user can radially squeeze or compress the lever arms 63 to release compression on the elastomeric seal 44 and increase the inner diameter 46 of the elastomeric seal 44 from the closed condition to a desired size of the inner diameter 46 based on an amount of radial squeeze.

As best shown in FIG. 7, a detachable cap 72 can be snapped or disposed over the second valve housing end 36 of the valve housing 32 to hold the pair of lever arms 63 in the radially compressed position when the medical valve assembly 10 is not in use. When the detachable cap 72 is in place, it keeps the elastomeric seal 44 in the open position, and thus increases the shelf life by reducing material creep, material sticking, and/or the distorting of the elastomeric seal 44.

Figure 5:
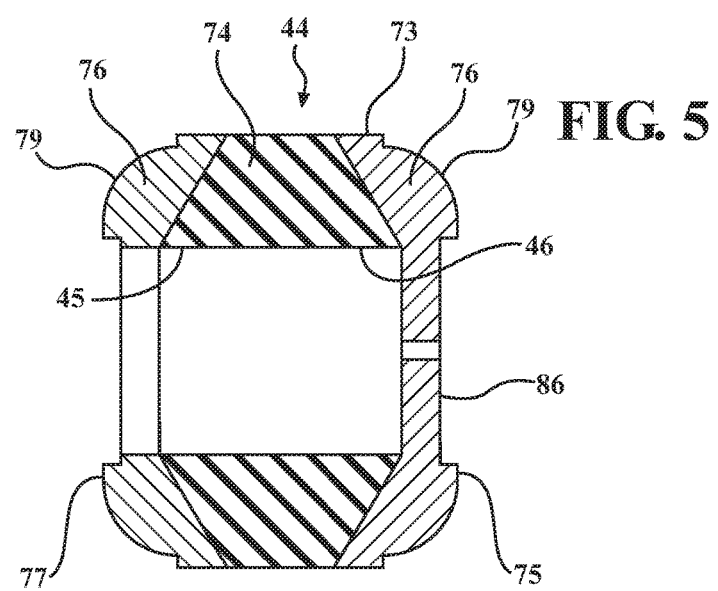
FIG. 5 is a partial view taken from FIG. 3 illustrating an elastomeric seal of the medical valve.
Figure 11A:
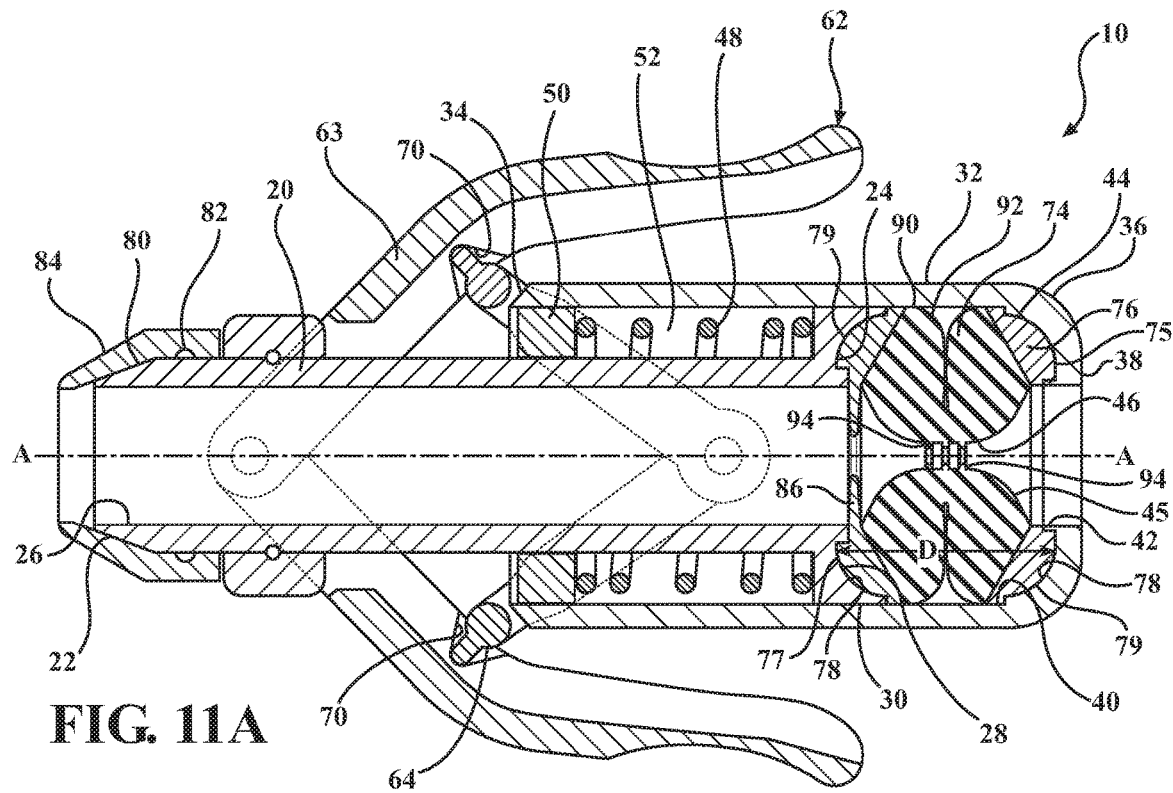
FIG. 11A is a cross-sectional view of the first embodiment of the medical valve illustrating an alternative arrangement of the elastomeric seal in the closed, or compressed, condition.
Figure 11B:
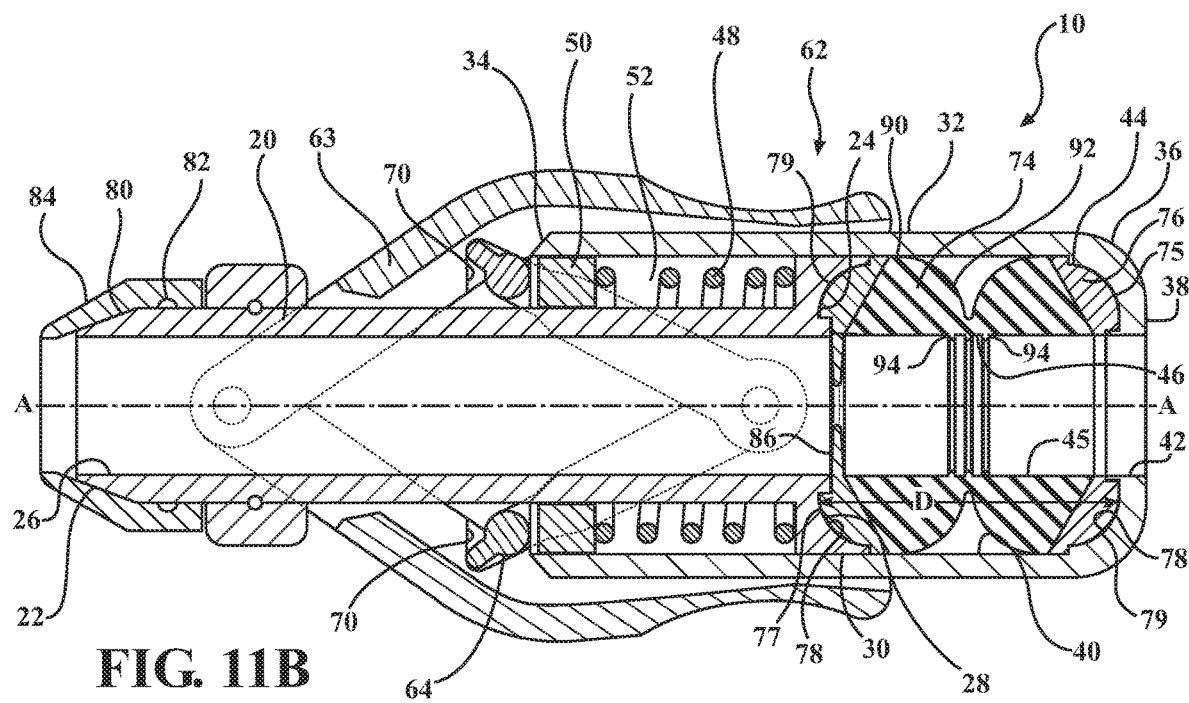
FIG. 11B is a cross-sectional view of the first embodiment of the medical valve illustrating the alternative arrangement of the elastomeric seal in the open, or non-compressed, condition.
Figure 12:
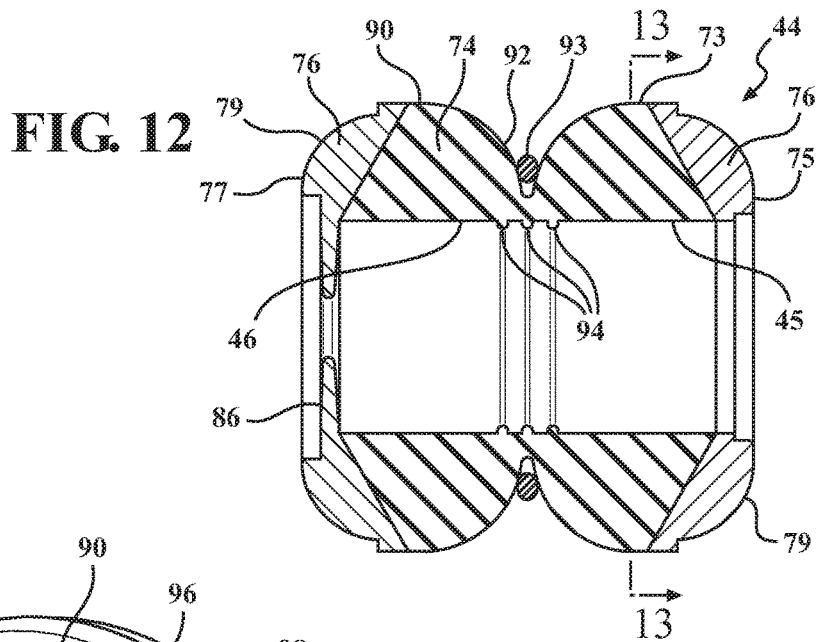
FIG. 12 is a cross-sectional view of the alternative arrangement of the elastomeric seal in the open, non-compressed condition.

As best shown in FIGS. 5 and 12, the elastomeric seal 44 includes a seal body 73 which extends around the axis A and includes an inner portion 74 and an outer portion 76 disposed axially outwardly from the inner portion 74. In other words, the seal body 73 extends from a proximal seal end 75 to a distal seal end 77 to define a pair of outer portions 76 disposed adjacent a respective one of the seal ends 75, 77, each separated by the inner portion 74. In a preferred embodiment, the inner portion 74 is made from a first material having a first durometer value and the outer portions 76 are made from a second material having a second durometer value being greater than the first durometer value. Thus, the elastomeric seal 44 preferably includes outer portions 76 that are harder than an inner portion 74. As further shown in FIGS. 4A, 4B, 11A and 11B, the outer portion 76 of the elastomeric seal 44 is disposed in compressed relationship between the plunger plate 28 and the flange 38. In a preferred embodiment, each of the pair of outer portions 76 of the elastomeric seal 44 define a curved outer surface 79 extending annularly around the axis A and disposed at respective proximal or distal ends 75, 77 of the elastomeric seal 44. Correspondingly, the plunger plate 28 and the flange 38 can include curved portions 78 which are disposed in mating or engaged relationship with respective curved outer surfaces 79 of the elastomeric seal 44 to improve the retention and compression of the outer portions 76 of the elastomeric seal 44 within the medical valve assembly 10.

As best shown in FIGS. 4, 11A and 11B, the tube 20 has a tapered portion 80 disposed adjacent the first tube end 22 for fitting a sheath over the tube 20. The tube 20 includes threads 82 disposed adjacent the first tube end 22 and a nose cap 84 is threadingly secured to the first tube end 22 for establishing a compression fit of the sheath between the nose cap 84 and the tapered portion 80 of the tube 20. Although not expressly shown, a wiper seal can be disposed within the passageway 26 between the elastomeric seal 44 and the first tube end 22 to provide a level of hemostasis around a larger device while the elastomeric seal 44 is opened for insertion of the medical device 12. Alternatively, as best shown in FIGS. 5, 11A, 11B and 12, a wiper seal 86 can be incorporated into the elastomeric seal 44 and extends radially inward from one of the outer portions 76. As best illustrated in FIG. 5, in one arrangement the wiper seal 86 can extend from the outer portion 76 disposed adjacent the proximal seal end 75 of the elastomeric seal 44. As best illustrated in FIGS. 11A, 11B and 12, in an alternative arrangement the wiper seal 86 extends from the outer portion 76 disposed adjacent the distal seal end 77 of the elastomeric seal 44. As a result, when the elastomeric seal 44 is inserted in the cavity 40, the wiper seal 86 is disposed adjacent the opening 42 of the valve housing 32.

As best illustrated in FIGS. 11B and 12, the inner portion 74 of the elastomeric seal 44 includes an outer surface 90 disposed opposite the inner surface 45. The inner portion 74 also defines an annular void 92 extending radially inwardly from the outer surface 90 and towards the inner surface 45 to remove or eliminate a portion of elastomeric material from the inner portion 74 of the elastomeric seal 44. As such, the annular void 92 decreases the requisite compressive force to compress the elastomeric seal 44 and effectuate a closing or decreasing of the inner diameter 46, such as illustrated in FIG. 11A. This advantageously allows the inner portion 74 of the elastomeric seal 44 to be comprised of an elastomeric material having a higher or increased durometer value relative to an elastomeric seal 44 lacking the annular void 92—which ultimately improves the durability of the elastomeric seal 44. In a preferred arrangement, the annular void 92 has a wedge cross-sectional shape in the non-compressed condition of the elastomeric seal 44, the cross-sectional view taken along a cross-sectional plane extending parallel to the axis A and between the proximal and distal seal ends 75, 77. This "wedge" shaped annular void 92 advantageously pushes bulk material of the inner portion 74 radially inwardly towards the axis A as the elastomeric seal 44 is compressed to further achieve a seal or closure of the inner diameter 46 under lower compression of the elastomeric seal 44. Put another way, the "wedge" shaped annular void 92 redirects a focal point of compression to the center of the elastomeric seal 44. As best illustrated in FIG. 12, a stability band 93—such as an appropriately sized o-ring—can be disposed or seated within the annular void 92 and extends annularly around the body of the elastomeric seal 44. The stability band 93 provides stability to the annular void 92 when medical devices are inserted or withdrawn through the elastomeric seal 44 to prevent side buckling of the elastomeric seal 44 that could result in a slight temporary leak.

As best illustrated in FIGS. 11A, 11B and 12, the inner portion 74 of the elastomeric seal 44 includes a plurality of ribs 94 extending radially inwardly from the inner surface 45 and encircling the axis A in concentric relationship with one another. During a compression of the elastomeric seal 44, the plurality of ribs 94 disposed around the inner surface 45 will shift inwards (i.e. radially towards the axis A) along with the inner portion 74 and touch off sooner than the inner portion 74, advantageously providing a seal or closure of the elastomeric seal 44 at lower compression. Furthermore, the utilization of multiple ribs 94 improves the sealing ability of the elastomeric seal 44 by providing additional sealing across each effective rib 94. As best illustrated in FIGS. 11A, 11B and 12, in a preferred arrangement, the plurality of ribs 94 includes three ribs 94 extending inwardly from the inner surface 45 and radially towards the axis A.

Figure 13:
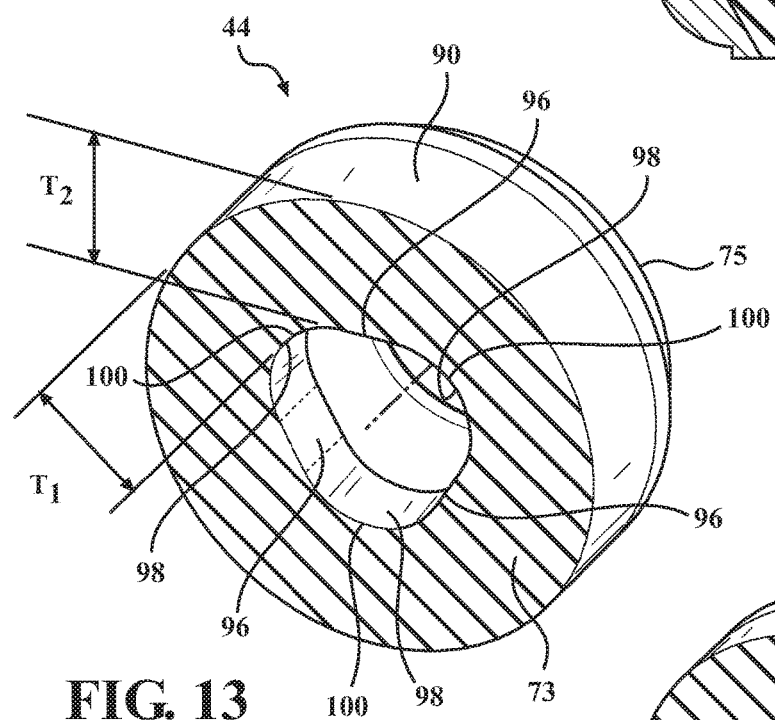
FIG. 13 is a perspective, cross-sectional view of the elastomeric seal in the open, non-compressed condition, taken along line 13-13 of FIG. 12 to illustrate an inner surface of the elastomeric seal having a plurality of planar portions and a plurality of radiused portions.
Figure 14:
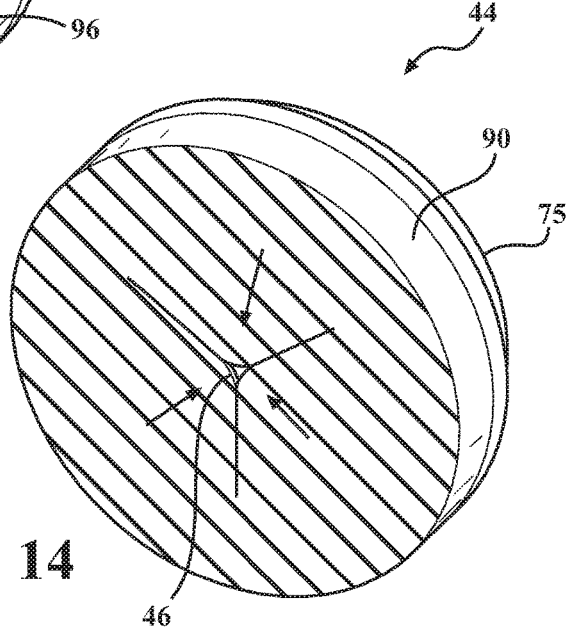
FIG. 14 is a perspective, cross-sectional view of the alternative arrangement of the elastomeric seal of FIG. 13 but shown in the closed, compressed condition to illustrate the inner surface compressed or closed along the plurality of planar portions.

As best illustrated in FIG. 13, the inner surface 45 of the elastomeric seal 44 (when disposed in the non-compressed condition) includes a plurality of planar portions 96 each extending generally parallel to the axis A and a plurality of radiused portions 98 being convex relative to the axis A, with adjacent ones of the plurality of planar portions 96 being interconnected with one of the plurality of radiused portions 98. In a preferred arrangement, the plurality of planar portions 96 includes three planar portions 96 and the plurality of radiused portions 98 includes three radiused portions 98 to define a generally triangular shape of the inner surface 45 of the elastomeric seal 44 when disposed in the non-compressed condition, the cross-sectional view taken along a plane which extends perpendicularly to the axis A and radially through the inner portion 74 of the elastomeric seal 44. The inner surface 45 of the elastomeric seal 44 advantageously allows the inner surface 45 to close shut and seal under less compression (less displacement and/or force) as compared to an inner surface 45 of the elastomeric seal 44 which lacks a plurality of planar portions and a plurality of radiused portions. Furthermore, the design of the inner surface 45 with alternating planar portions 96 and radiused portions 98 improves reliability of the elastomeric seal 44 by providing a more consistent and predictable closure or sealing during an establishment of the closed condition of the medical valve assembly 10. For example, as illustrated and highlighted in FIG. 14 by the arrows, the arrangement of the inner surface 45 causes the elastomeric seal 44 to buckle or collapse radially inwardly towards the axis A along each of the plurality of planar portions 96. Once the initial buckle or collapse occurs in response to a compression force exerted by the compression member 48, the buckling or collapsing pattern is maintained throughout a compression or closure of the elastomeric seal 44, thus providing for a predictable closure of the elastomeric seal 44.

As further illustrated in FIG. 13, the elastomeric seal 44 has a first thickness $T_1$ extending between an apex 100 defined by each of the radiused portions 98 of the inner surface 45 and the outer surface 90. The apex 100 is defined by a point along each of the radiused portions 98 which is disposed farthest radially away from the axis A. The elastomeric seal 44 also has a second thickness $T_2$ extending between the planar portions 96 of the inner surface 45 and outer surface 90, with the second thickness $T_2$ being greater than the first thickness $T_1$. The alternating thin and thick regions of the elastomeric seal 44 as the seal body 73 extends around the axis A further assist in a predictable closure during compression by the compression member 48 because the thinner sections of the elastomeric seal 44 (as defined between the apex 100 of each of the radiused portions 98 and the outer surface 90) will crease under lower compression relative to the stiffer, thick sections (as defined between the planar portions 96 and the outer surface 90). Accordingly, the alternating thickness of the elastomeric seal 44 also improves reliability of both elastomeric seal 44 as well as the medical valve assembly 10 into which it is incorporated.

It will be appreciated by those skilled in the art that the medical valve assembly 10' shown in FIGS. 8 and 9 can be equipped with the compression type manual actuator 62 shown in FIGS. 3, 4 and 7 or, in the alternative, the pull-type manual actuator 60 shown in FIG. 6. Likewise, alternative configurations are contemplated for manual actuators that function to controllably vary the relative axial position between two components for proportionately controlling the compression load applied to an elastomeric seal to regulate an internal opening dimension defined thereby.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A medical valve assembly for use in inserting a medical device into a body vessel of a patient, comprising:
    a tube extending between a first tube end and a second tube end along an axis;
    a plunger plate extending radially from said second tube end of said tube;
    a valve housing surrounding said tube about said second tube end and extending from a first valve housing end to a second valve housing end; said valve housing including a flange extending radially inwards from said second valve housing end and disposed in spaced relationship with said plunger plate to define a distance extending therebetween;
    an elastomeric seal extending between said plunger plate and said flange and having an inner surface defining an inner diameter for use in establishing a variable seal of the medical valve assembly; a compression member disposed within said valve housing and biased against said plunger plate for compressing said elastomeric seal from a non-compressed condition to a compressed condition to decrease said inner diameter and establish a closed condition of the medical valve; and
    said inner surface of said elastomeric seal in said non-compressed condition having a plurality of planar portions and a plurality of radiused portions with adjacent ones of said plurality of planar portions interconnected with one of said plurality of radiused portions.

2. A medical valve assembly as set forth in claim 1, wherein said plurality of planar portions includes three planar portions and said plurality of radiused portions includes three radiused portions to define a generally triangular shaped inner surface as viewed in cross-section.

3. A medical valve assembly as set forth in claim 1, further comprising:
    said elastomeric seal extending between a proximal seal end disposed in abutting relationship with said flange and a distal seal end disposed in abutting relationship with said plunger plate; said elastomeric seal having an outer surface disposed radially outwardly from said inner surface; and
    said elastomeric seal in said non-compressed condition having a first thickness extending between an apex defined by each of said plurality of radiused portions and said outer surface and a second thickness extending between each of said plurality of planar portions and said outer surface, with said second thickness being greater than said first thickness.

4. A medical valve assembly as set forth in claim 3, wherein said elastomeric seal includes a plurality of ribs extending radially inwardly from said inner surface and encircling said axis A in concentric relationship with one another.

5. A medical valve assembly as set forth in claim 4, wherein said plurality of ribs includes three ribs.

6. A medical valve assembly as set forth in claim 4, wherein said elastomeric seal defining an annular void extending radially inwardly from said outer surface towards said inner surface to decrease a requisite compression force for effectuating said decreased inner diameter of said elastomeric seal.

7. A medical valve assembly as set forth in claim 6, wherein said annular void in said non-compressed condition of said elastomeric seal being wedge-shaped as viewed in cross-section.

8. A medical valve assembly as set forth in claim 7, further comprising a stability band seated within said wedge-shaped annular void and extending annularly around said elastomeric seal.

9. A medical valve assembly as set forth in claim 3, wherein each of said proximal and distal seal ends of said elastomeric seal define a curved outer surface extending annularly around said axis A, and wherein said plunger plate and said flange each define respective curved portions disposed in mating or engaged relationship with a respective one of said curved outer surfaces of said elastomeric seal to improve a retention and compression of said elastomeric seal within the medical valve assembly.

10. A medical valve assembly as set forth in claim 1, wherein one of said valve housing and said tube is axially movable relative to the other via a manual actuator connected to said valve housing to vary the distance between said plunger plate and said flange and adjust said inner diameter of said elastomeric seal for variably sealing the medical valve assembly to a variety of differently sized medical devices.

11. An elastomeric seal for use with a medical valve assembly, comprising:
a seal body extending along an axis A between a proximal seal end and a distal seal end;
said seal body having an inner surface extending around said axis A and an outer surface disposed radially outwardly from said inner surface;
said inner surface having a plurality of planar portions each extending generally parallel to said axis and a plurality of radiused portions each being convex relative to said said axis, with adjacent ones of said plurality of planar portions interconnected with one of said plurality of radiused portions.

12. An elastomeric seal as set forth in claim 11, wherein said plurality of planar portions includes three planar portions and said plurality of radiused portions includes three radiused portions to define a generally triangular shaped inner surface of the elastomeric seal as viewed in cross-section.

13. An elastomeric seal as set forth in claim 11, wherein said seal body having a first thickness extending between an apex of said plurality of radiused portions and said outer surface and a second thickness extending between each of said plurality of planar portions and said outer surface, with said second thickness being greater than said first thickness.

14. An elastomeric seal as set forth in claim 11, further comprising a plurality of ribs extending radially inwardly from said inner surface and encircling said axis A in concentric relationship with one another.

15. An elastomeric seal as set forth in claim 14, wherein said plurality of ribs includes three ribs.

16. An elastomeric seal as set forth in claim 14, wherein said seal body defining an annular void extending radially inwardly from said outer surface towards said inner surface to decrease a requisite compression force for compressing the elastomeric seal to effectuate a closure of the elastomeric seal.

17. An elastomeric seal as set forth in claim 16, wherein said annular void being wedge-shaped as viewed in cross-section.

18. An elastomeric seal as set forth in claim 17, further comprising a stability band seated within said wedge-shaped annular void and extending annularly around said seal body.

19. An elastomeric seal as set forth in claim 11, wherein each of said proximal and distal seal ends of said elastomeric seal define a curved outer surface extending annularly around said axis A.

20. A medical valve as set forth in claim 11, wherein said elastomeric seal includes an outer portion disposed adjacent each of said proximal seal ends and an inner portion disposed between said outer portions, and said inner portion having a first durometer value and said outer portion having a second durometer value being greater than said first durometer value.

* * * * *